(12) United States Patent
Fändrich

(10) Patent No.: US 12,343,395 B2
(45) Date of Patent: *Jul. 1, 2025

(54) REGULATORY MACROPHAGES FOR TREATING ANGIOPATHIES

(71) Applicant: Trizell GmbH, Hamburg (DE)

(72) Inventor: Fred Fändrich, Kiel (DE)

(73) Assignee: Trizell GmbH, Hamburg (DE)

( * ) Notice: Subject to any disclaimer, the term of this patent is extended or adjusted under 35 U.S.C. 154(b) by 59 days.

This patent is subject to a terminal disclaimer.

(21) Appl. No.: 18/296,065

(22) Filed: Apr. 5, 2023

(65) Prior Publication Data

US 2023/0233604 A1    Jul. 27, 2023

Related U.S. Application Data

(63) Continuation of application No. 16/647,121, filed as application No. PCT/EP2018/074663 on Sep. 12, 2018, now Pat. No. 11,648,266.

(30) Foreign Application Priority Data

Sep. 13, 2017 (EP) ..................... 17190982

(51) Int. Cl.
| | | |
|---|---|---|
| A61K 40/17 | (2025.01) | |
| A61K 9/00 | (2006.01) | |
| A61K 40/22 | (2025.01) | |
| A61K 40/24 | (2025.01) | |
| A61K 40/40 | (2025.01) | |
| A61K 40/41 | (2025.01) | |
| A61P 17/02 | (2006.01) | |
| C12N 5/0786 | (2010.01) | |

(52) U.S. Cl.
CPC .............. *A61K 40/17* (2025.01); *A61K 40/22* (2025.01); *A61K 40/24* (2025.01); *A61K 40/40* (2025.01); *A61K 40/416* (2025.01); *A61P 17/02* (2018.01); *C12N 5/0645* (2013.01); *A61K 9/0019* (2013.01); *A61K 2239/38* (2023.05)

(58) Field of Classification Search
None
See application file for complete search history.

(56) References Cited

U.S. PATENT DOCUMENTS

2020/0299647 A1* 9/2020 Hutchinson ............... A61P 9/10

* cited by examiner

*Primary Examiner* — Daniel C Gamett
(74) *Attorney, Agent, or Firm* — Hovey Williams LLP; Crissa A. Cook

(57) ABSTRACT

The present invention relates to the use of immunoregulatory macrophages for treating diseases that are associated with pathological changes of the blood vessels. The present invention particularly relates to the use of immunoregulatory macrophages for treating micro- and macroangiopathies of the lower limbs. The invention furthermore relates to the use of immunoregulatory macrophages for promoting tissue remodelling to facilitate wound healing. Pharmaceutical compositions for use in the recited treatments are also disclosed which comprise the immunoregulatory macrophages.

15 Claims, 8 Drawing Sheets

CD258/TNFSF14

IDO

REGULATORY MACROPHAGES FOR TREATING ANGIOPATHIES

CROSS-REFERENCE TO RELATED APPLICATIONS

This application is a continuation of U.S. Ser. No. 16/647,121, filed Mar. 13, 2020, which is the U.S. National Stage of International Patent Application No. PCT/EP2018/074663, filed Sep. 12, 2018, which are hereby incorporated by reference in their entireties, and which claim priority to European Patent Application No. 17190982.3, filed Sep. 13, 2017.

FIELD OF THE INVENTION

The present invention relates to the use of immunoregulatory macrophages for treating diseases that are associated with pathological changes of the blood vessels. The present invention particularly relates to the use of immunoregulatory macrophages for treating micro- and macroangiopathies of the lower limbs. The invention furthermore relates to the use of immunoregulatory macrophages for promoting tissue remodelling to facilitate wound healing. Pharmaceutical compositions for use in the recited treatments are also disclosed which comprise the immunoregulatory macrophages.

TECHNICAL BACKGROUND

Vascular ulcers of the lower limbs cause severe problems for patients and health care systems. Leg ulcers may be acute or chronic. Acute leg ulcers are sometimes defined as those that follow the normal phases of healing; they are expected to show signs of healing in less than 4 weeks and include traumatic and postoperative wounds. Chronic leg ulcers are those that persist for longer than 4 weeks and are often of complex poorly understood origin. Chronic leg ulcers commonly occur in patients suffering from diabetes.

Minimally invasive methods of managing incompetence of superficial saphenous trunks, including endovenous laser ablation, radiofrequency ablation, and foam sclerotherapy have been used for treating patients with leg ulcers. In addition, perforating vein ligation is commonly combined with superficial venous surgery for leg ulcer patients, but effectiveness of this method is currently unsatisfactory. A small number of drugs have been shown to be beneficial in promoting leg ulcer healing; however, healing of leg ulcers remains complicated and relapses are quite commonly observed.

Despite progress made in the field of leg ulcer treatment, there remains an ongoing need to provide further compounds and methods that for treating acute or chronic leg ulcers, and in particular chronic leg ulcers. It has now been surprisingly found that certain immunoregulatory cells can be used for treating chronic wounds, such as diabetic leg ulcers. As will be shown herein, administration of such cells directly into chronic wounds and their proximity results in accelerated healing.

The use of immunoregulatory cells for the treatment of certain diseases has received serious attention in recent years, in particular for establishing immunologic tolerance in a recipient receiving these cells [1]. Presently, several immunoregulatory cell types are reaching the point of pre-clinical development, which will allow them to be investigated as immunosuppressive agents in early-phase clinical trials, including regulatory T cells [2], tolerogenic dendritic cells [3] and regulatory macrophages [4].

It has been contemplated to use immunoregulatory cells for treating a number of immunologic conditions, including T cell- and B cell-mediated autoimmune disease, chronic inflammatory disorders, graft-versus-host disease (GVHD), and transplant rejection. In these conditions, cell-based immunoregulatory therapies are intended to reduce or even obviate the need for general immunosuppressive or anti-inflammatory therapy, thereby sparing patients its attendant complications. Because the kind of immunologic tolerance supported by regulatory cells is dominant and self-sustaining, there exists the possibility that cell-based immunotherapy may offer a curative option in diseases that would otherwise require long-term general immunosuppressive or anti-inflammatory therapy.

One particularly promising candidate cell type for use as an adjunct immunosuppressive agent in transplantation and other clinical indications is the immunoregulatory macrophage (referred to herein and in the literature as "Mreg"). The Mreg cell reflects a unique state of macrophage differentiation, which is distinguished from macrophages in other activation states by its robust phenotype and potent T-cell suppressor function [5]. Human Mregs potently suppress mitogen-stimulated T-cell proliferation in vitro, which can be attributed to interferon (IFN) γ-induced indoleamine 2,3-dioxygenase activity, as well as contact-dependent deletion of activated T cells.

In addition, Mregs drive the development of activated induced regulatory T cells that, in turn, suppress the proliferation of effector T cells and inhibit the maturation of dendritic cells. Therefore, when Mregs are administered to a recipient, it is hypothesized that a feed-forward loop of immunologic regulation is initiated leading to the long-term, antigen-specific immunological hyporesponsiveness.

Mreg-containing cell preparations have already been used in clinical trials and were administered to a total of 19 kidney transplant recipients as a form of adjunct immunosuppressive treatment in a series of case studies and two early-phase clinical trials [5]-[9]. These pilot studies clearly demonstrate the feasibility of this technique for solid organ transplantation. An additional two living-donor kidney transplant recipients have now been treated with approximately $8.0 \times 10^6$ cells/kg of pure donor-derived Mregs [5]. An additional clinical trial of Mreg therapy in living-donor renal transplantation now has regulatory approval within the framework of the ONE Study (Clinicaltrials.gov: NCT02085629). This trial aims to treat 16 patients with donor-derived Mreg cells at a dose of $2.5 \times 10^6$ to $7.5 \times 10^6$/kg body weight under cover of 500 mg/day mycophenolate mofetil on day 7 before surgery. Treatment of ulcers by Mregs have not been contemplated in the prior art before and makes a significant contribution to managing leg ulcers.

DESCRIPTION OF THE INVENTION

The invention is based on the insight that Mreg cells prepared in accordance with established protocols accelerate the healing of leg ulcers, in particular chronic leg ulcers. Therefore, in a first aspect the present invention relates to an immunoregulatory macrophage expressing the markers CD258, DHRS9 and IDO for use in a method of treating micro- and macroangiopathies of the lower limbs in a subject.

As used herein, a microangiopathy is a blood vessel disease which affects small blood vessels and capillaries in the body, such as small cerebral vessels, small coronary vessels or small vessels in the legs. During microangiopathy, the capillary basement membrane becomes thick and hard which causes obstruction or rupture of capillaries or small arteries which in turn results in tissue necrosis and loss of function. In contrast, a macroangiopathy is a blood vessel disease that affects large blood vessels, such as the arteries. Obstruction of the larger arteries leads to high incidence of heart attacks, strokes and peripheral vascular disease in diabetics. Obstruction of the arteries in the leg often results in ulcers on the feet and legs that slowly heal. Peripheral vascular disease also causes intermittent claudication, i.e., pain during walking, which severely impairs mobility. In a lot of cases, macroangiopathies required amputation of one or both legs, in particular in diabetic patients.

One cause of micro- and macroangiopathies is long-term diabetes mellitus. In diabetic patients, high blood glucose levels cause the endothelial cells of the blood vessels to absorb more glucose than normal. These cells then form more glycoproteins on their surface than normal, and also cause the basement membrane in the vessel wall to grow abnormally thicker and weaker. As a result, the vessel wall become leaky and slow the flow of blood through the body such that some tissues do not receive sufficient oxygen an hour damaged.

According to the invention, the microangiopathy to be treated is preferably selected from the group of diseases consisting of angiitis, arteritis, angiodysplasia, atrophy blanche, dermatosclerosis, Determann syndrome, diabetic angiopathy, endangiitis obliterans, erythromelalgia, fibro muscular dysplasia, malum perforans, Mönckeberg Sclerosis, Osler's disease, compartment syndrome, Paget-von-Schroetter syndrome, Raynaud's syndrome, and leg ulcers. In a particularly preferred aspect, the micro- or macroangiopathies which are to be treated according to the invention are leg ulcers. As used herein, leg ulcers include diabetic leg ulcers and venous leg ulcers.

According to the invention, the macroangiopathy to be treated is preferably selected from the group of aneurysm, dissection, atherosclerosis, atherothrombosis, peripheral arterial occlusive disease (PAD), claudicatio intermittens, necrosis and gangrene, vascular malformation, Leriche syndrome, or compression syndrome.

In practise, the immunoregulatory macrophages will be formulated as a pharmaceutical composition. The pharmaceutical composition will comprise, as a first component, an effective amount of Mreg cells or a sub-cellular fraction thereof. As used herein, an effective amount of Mreg cells to be administered to the patient will be in the range of about $1\times10^4$ to about $1\times10^8$/kg body weight, preferably between about $1\times10^5$ and about $1\times10^7$/kg body weight, and more preferably between about $1\times10^6$ and about $9\times10^6$/kg body weight, such as about $1\times10^6$/kg, about $2\times10^6$/kg, about $3\times10^6$/kg, about $4\times10^6$/kg, about $5\times10^6$/kg, about $6\times10^6$/kg, about $7\times10^6$/kg, or about $8\times10^6$/kg body weight of the patient to be treated.

Similarly, where the invention comprises the administration of sub-cellular fractions of the Mreg cells, these fractions will preferably be prepared based on an amount of Mreg cells that corresponds to one of the ranges mentioned above in connection with the administration of cells. As used herein, a sub-cellular fraction of the Mreg cell may include necrotic cell particles, apoptotic cell particles, or exosomes. Cell lysates prepared by treating cells with hypoosmotic solutions, dissolution using detergents or acids, freeze-thawing or heating, sonication, irradiation, mechanical disruption or prolonged storage may also be used. Sub-cellular fractions may also include cell extracts containing total cellular protein, membrane proteins, cytoplasmic proteins or purified MHC molecules.

Apart from the Mregs cells or their sub-cellular fractions, the pharmaceutical composition can comprise further excipients, such as buffers, pH regulating agents, preservatives, and the like.

The nature and amounts of the excipients included into the pharmaceutical composition will depend on the intended route of administration.

Generally, different routes of administration are feasible for providing the Mreg cells or sub-cellular fractions thereof to a patient in need of treatment. Preferably, the pharmaceutical composition of the invention will be formulated for parenteral administration, such as subcutaneous, intramuscular, intravenous or intradermal administration. In one embodiment, the Mreg cells or sub-cellular fractions thereof or a composition comprising said cells or fractions are administered to the patient by intravenous administration, e.g., by injection or infusion. Pharmaceutical compositions suitable for intravenous administration by injection or infusion normally include sterile aqueous solutions or suspensions and sterile powders for the extemporaneous preparation of sterile solutions or suspensions. The formulation of the Mreg cells or their sub-cellular fractions into pharmaceutical compositions can be achieved by applying routine methods known in the field of drug formulation. Suitable methods are described, for example, in standard textbooks.

For administration by injection or infusion, suitable carriers may comprise physiological saline, bacteriostatic water, Cremophor ELTM (BASF) or phosphate buffered saline (PBS). The carrier may also be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Sterile injectable solutions can be prepared by incorporating the cells or sub-cellular fractions in the required amount in an appropriate solvent with one or more of the above mentioned ingredients followed by sterile filtration. Generally, suspensions are prepared by incorporating the active compound, i.e., the cells or sub-cellular fractions thereof, into a sterile vehicle that contains a basic dispersion medium and the required other ingredients from those mentioned above. In case of sterile powders for the preparation of sterile injectable solutions, methods of preparation are vacuum drying and freeze-drying that yields a powder of the cells or sub-cellular fractions thereof plus any additional desired ingredient from a previously sterile-filtered solution thereof. The pharmaceutical composition should be stable upon administration and is preferably preserved against the contaminating action of microorganisms, such as bacteria and fungi, for example, by including parabens, chlorobutanol, phenol, ascorbic acid, thimerosal, and the like into the composition.

Where the pharmaceutical composition is intended for injection, the total volume to be injected is between 1 and 100 ml, preferably between 10 and 50 ml, such as 20 ml, 30 ml or 40 ml. Where the pharmaceutical composition is intended for infusion, the total volume to be infused will be between 50 and 500 ml, wherein a volume of between 90 ml and 250 ml is particularly preferred, and wherein a volume of between 90 ml and 150 ml is even more preferred.

The Mreg cells can be administered to a patient in need of treatment by different administration regimens. For example, where the cells or cell fractions are administered to the patient by intravenous infusion, the total amount of Mreg cells or cell fractions to be administered can be supplied by one or more than one infusion. In a preferred embodiment, the Mreg cells or cell fractions are supplied to the patient through an infusion set with a 200 μm filter. The suspension comprising the Mreg cells or cell fractions may be primed with 0.9% NaCl. The suspension may be given in a single infusion, more preferably a short-term infusion within less than 60 min, e.g., within 60 min, 30 min, 20 min or 15 min. Preferably, a central venous catheter is used for administering the Mreg cell suspension.

The administration of the Mreg cells or cell fractions can be accompanied by the preceding, simultaneous or subsequent administration of other active agents. For example, where the Mreg cells or cell fractions are administered to patients suffering from Micro- or macroangiopathies, compounds against blood hyperviscosity, such as calcium dobesilate, compounds which exert a capillary stabilizing effect, such as naftazone, or the like can be administered before, simultaneously with or after Mreg administration.

Although the Mreg cells obtained from the method described in the first aspect of the invention exhibit a stable phenotype, it is recommended for safety reasons that the Mreg cells or sub-cellular fractions obtained from the Mreg cells are administered within 24 hours after harvesting them from the cell cultures. Preferably, the cells are administered within 20 hours, within 16 hours, within 12 hours, within 8 hours, or within 4 hours after harvesting the cells from the cultures.

In another aspect, the invention relates to an immunoregulatory macrophage for use in a method of promoting surgical, traumatic or other wound healing in a subject. Mreg therapy may be used to promote healing of acute or chronic wounds, optionally in conjunction with conventional management (i.e., cleaning, closure and dressing). Wounds may be open or closed. Open wounds may include incisions, lacerations, abrasions, avulsions, penetrating injuries or punctures. Closed wounds may include crush injuries or haematomas. Incisions may be traumatic or iatrogenic (i.e., surgical incisions). Mregs may be used to promote engraftment of autologous or allogeneic skin grafts. Mregs may be used in conjunction with conventional management may accelerate healing of burns, which may be caused by exposure of skin to heat, extreme cold, chemicals, friction, radiation or electrical current. The statements made in connection with the treatment of ulcers likewise apply to the treatment of wounds or burns.

The preparation of Mregs for use in the methods of the present invention has been extensively described in the literature. Mreg cells are derived from human CD14+ blood monocytes. In order to induce the characterizing biological properties of Mreg cells, the monocytes are treated with a specific combination of growth factors, cytokines and receptor ligands. The cells obtained from this process are characterized by a unique phenotype that distinguishes them from blood monocytes, other types of monocyte-derived macrophages, monocyte-derived dendritic cells and other suppressive myelomonocytic cell products.

A suitable process for preparing Mregs comprises:
(a) isolating CD14 positive monocytes from a blood sample of a subject;
(b) culturing the monocytes in a culture medium containing
  (i) M-CSF and/or GM-CSF, and (ii) a ligand of CD16;
(c) contacting the cells with IFN-γ; and
(d) obtaining the Mreg cell from the culture medium.

The method uses blood monocytes as starting material. While it will be preferred that the method is used for generating Mreg cells from human blood monocytes, the method is not limited to the differentiation of cells of human origin. In fact, it is applicable also to other types of non-human cells, in particular vertebrate cells, e.g., non-human primate or pig cells.

The method may be used to differentiate CD14 positive monocytes of a human donor into Mregs. The monocytes which serve as a starting material for the method of the invention are obtained from the peripheral blood of a human donor. The donor may be a healthy subject or a patient suffering from one or more diseases. The monocyte donor may be the intended recipient of the differentiated Mreg cells (autologous approach). Alternatively, the monocyte donor may be a separate person from the intended recipient of the differentiated Mreg cells (allogeneic approach). In the latter case, the donor and recipient may be genetically related or unrelated. The preferred relationship between donor and recipient depends upon the intended clinical application. The use of autologous Mreg cells may help to avoid certain adverse reactions. Therefore, the use of autologous Mreg cells is normally preferred.

Different methods are known in the art for the enrichment of mononuclear cells from peripheral blood, and each of these methods can be used in the context with the above preparation method. For example, blood obtained by venepuncture can be treated with an anticoagulant and subsequently separated by use of a separation medium, such as Ficoll-Paque Plus. For this, the anticoagulant-treated blood sample is layered on the Ficoll-Paque Plus solution and centrifuged, which will result in the formation of layers containing the different cell types. The bottom layer contains erythrocytes which have been aggregated and sedimented by the Ficoll-Paque Plus reagent. The layer immediately above the erythrocyte layer contains mostly granulocytes which have migrated through the Ficoll-Paque Plus layer. Owing to their lower density, monocytes and lymphocytes are found at the interface between the plasma and the Ficoll-Paque Plus. Enrichment of the mononuclear cell fraction can be achieved by isolation of the layer and subsequent washing and centrifugation.

Another routinely used method for separating mononuclear leucocytes from blood samples includes leukapheresis. Leukapheresis is a specific type of apheresis in which white blood cells are obtained from peripheral blood according to their relative densities in a continuous process. In this procedure, the blood of a subject is passed through a special centrifugation device which collects the chosen fraction of white blood cells and returns the remaining blood cells and plasma back to the donor. Leukapheresis is nowadays a routine clinical measure for obtaining leucocytes or stem cells from peripheral blood. Different devices are available from several manufactures that can be used for performing leukapheresis in the context with the present invention, e.g., the Spectra Optia® Apheresis System from Terumo BCT. Where the leukapheresis is carried out by use of the COBE® Spectra Apheresis System, it is preferred to use the manual protocol provided by the manufacturer, since this protocol was found to result in better quality monocytes compared to the AutoPBSC protocol.

Both the use of a separation medium like Ficoll-Paque Plus and the use of a leukapheresis device will provide a cell fraction that contains, apart from the monocytes, also lymphocytes. According to the invention, monocytes may be enriched and separated from the lymphocytes by known methods, e.g., by magnetic bead separation, sorting by flow cytometry, elutriation, filtration or plastic adherence, before the cells are introduced into the Mreg preparation method. However, it is not mandatory to use a homogeneous monocyte fraction in the Mreg preparation method. In fact, the presence of an amount of 0.1-20%, preferably 10-20% lymphocytes in the monocyte fraction may positively influence the differentiation of monocytes to Mregs.

For obtaining a mononuclear cell preparation that is enriched for monocytes, peripheral blood mononuclear cells may be contacted, e.g., with CD14 microbeads to which CD14-positive monocytes bind. The monocytes in step (a) of the above method may be isolated by leukapheresis and subsequently subjected to separation step using CD14 affinity molecules, preferably CD14 antibodies. Such a purification step massively reduces contamination of the starting material with non-monocytes. Reduction of T cell contamination is very valuable from a patient safety perspective because it minimizes the potential risk of donor-versus-recipient reactions. The isolation of the CD14 monocytes can be assisted by automated isolation systems. For example, the CD14 monocytes to be used in the method of the invention can be isolated with the CliniMACS® Technology (Miltenyi Biotec GmbH, Bergisch Gladbach, Germany).

The monocyte fraction, which has been isolated by leukapheresis and/or other methods, can directly be used for differentiation by incubation with M-CSF and/or GM-CSF and the CD16 ligand, or it can be stored in autologous plasma supplemented with Anticoagulant Citrate Dex-trose Solution (ACD-A) or any other suitable buffer until further use. If the isolated monocyte fraction has to be transported to a different site where the differentiation process is carried out, care should be taken that differentiation of the cells by incubation with M-CSF/GM-CSF is started within 24 hours after isolation of the cells, preferably within 18 hours, within 12 hours, within 6 hours, within 4 hours, or within 2 hours after isolation of the monocytes. For long term storage, the monocyte fraction may be resuspended in a suitable cryopreservation solution and stored at temperatures below 20° C., preferably below 80° C. for extended periods of time.

After isolation of the monocytes, the cells are incubated in the presence of M-CSF/GM-CSF and a CD16 ligand. For example, the cells may be suspended in a medium that contains M-CSF and/or GM-CSF and a CD16 ligand. Alternatively, it is also possible to add M-CSF/GM-CSF and the CD16 ligand some time after start of cell culturing. The culture medium used in step (b) of the above method can be any medium that has been described in the literature as suitable for use in the culturing of monocytes and/or macrophages. Suitable culturing media include, for example, the PromoCell Macrophage Generation Medium (PromoCell GmbH, Heidelberg, Germany), Dulbecco's modified Eagle's medium (DMEM), DMEM:F12 blend, Medium 199, or RPMI-1640 medium. The culture medium preferably is a chemically defined medium. Apart from M-CSF/GM-CSF, the culture medium can contain other factors to promote the survival and differentiation of Mregs, including: growth factors and cytokines, such as epidermal growth factor (EGF), or IL-4; fatty acids, cholesterol and other lipids; vitamins, transferrin and trace elements; insulin, glucocorticoids, cholecalciferol or ergocalciferol, and other hormones; non-specific immunoglobulin and other plasma proteins. In a preferred embodiment of the invention, the culture medium is RPMI-1640 or a medium derived therefrom.

The culture medium used for incubating the isolated CD14 positive monocytes may contain Macrophage Colony-Stimulating Factor (M-CSF, also known as CSF1), Granulocyte Macrophage Colony-Stimulating factor (GM-CSF), or both. M-CSF is known in the art as a hematopoietic growth factor that influences the proliferation, differentiation, and survival of monocytes, macrophages, and bone marrow progenitor cells. Granulocyte-macrophage colony-stimulating factor (GM-CSF, also known as CSF2), is a monomeric glycoprotein that functions as a cytokine and is secreted by macrophages, T cells, mast cells, NK cells, endothelial cells and fibroblasts. M-CSF and GM-CSF proteins from different species have been described and can be purchased from different manufacturers. The choice of the M-CSF and/or GM-CSF will depend on the origin of the monocytes which are to be differentiated into Mreg cells. For example, if human monocytes are differentiated to Mregs using the process described above, the medium used will contain human M-CSF and/or human GM-CSF, preferably recombinant human M-CSF and/or recombinant human GM-CSF. Similarly, if porcine monocytes are used in the differentiation method, the M-CSF and/or GM-CSF added to the medium will be of porcine origin.

Usually, the concentration of M-CSF in the culture medium in step (b) of the above method is in the range of 1-100 ng protein per ml medium. Time-course experiments to measure the amount of M-CSF in the culture medium revealed that M-CSF was consumed or degraded over time, such that cultures with an initial dose of 5 ng/ml M-CSF contained sub-physiological concentrations by day 2 of culturing; in contrast, cultures with an initial dose of 25 ng/ml M-CSF maintained concentrations of >10 ng/ml throughout a 7-day culturing period. Thus, the concentration of M-CSF in the culture medium will normally be in the range of 20-75 ng/ml, such as 20-25 ng/ml. Where GM-CSF is used instead of M-CSF, the same concentrations can be used in the medium as outlined above in the context with M-CSF. Since GM-CSF appears to be more potent compared to M-CSF, a concentration of GM-CSF of 0.1-100 ng protein per ml medium is suggested. In cases where both M-CSF and GM-CSF are used in the medium, the overall concentrations of these two growth factors will be in the above-mentioned range, i.e., in the range of 20-75 ng/ml.

Apart from the M-CSF and/or GM-CSF, the culture medium used in step (b) of the above method also comprises a CD16 ligand. Stimulation of the CD16 cell surface receptor on the monocytes is required to induce their differentiation into Mreg cells. Stimulation of the CD16 cell surface receptor can be achieved by the addition of a human or non-human immunoglobulin, and more preferably a human immunoglobulin, or a fragment thereof. The immunoglobulin fragment can be, for example, an Fc fragment of an immunoglobulin. It is assumed that the immunoglobulin acts through FcγRIII (CD16) to induce the Mreg phenotype. A simple way to achieve stimulation of the CD16 ligand is the addition of human serum to the culture medium. Thus, the medium used for generating the Mreg cells may contain 1-20% human AB serum.

Where the Mregs cells are intended for use in therapeutic applications in which the induction of angiogenesis is desired, the medium used for culturing the monocytes in step (b) of the method of the invention may comprise, apart from M-CSF/GM-CSF and the CD16 ligand, a toll-like receptor (TLR) ligand, such as lipolysaccharide (LPS), monophosphoryl lipid A (MPLA) or High Mobility Group Box protein 1 (HMGB1) to enhance the production of angiogenic factors like VEGF-A. The TLR ligand can be added to the culture medium in a concentration range of 1000 ng/ml to 1 µg/ml. The TLR ligand can be added at any stage of the production method. It can be present in the initial medium which is used for culturing the monocytes, i.e., at day 0 of the culture, or it can be added at a later stage, e.g., at day 5, 6 or 7 of the culture. Preferably, the TLR ligand is added simultaneously with the addition of the IFN-γ.

In step (c) of the method of the invention, the cells are contacted with the cytokine interferon gamma (IFN-γ). The choice of the IFN-γ used in the method of the invention will depend on the origin of the monocytes which are subjected to the method of the invention. If human monocytes are differentiated to Mregs, the IFN-γ added will normally be recombinant human IFN-γ. The amount of IFN-γ to be added to the monocyte culture will be in the range of 5-100 ng/ml. An amount of 25 ng IFN-γ per ml culture medium is particularly suitable.

The IFN-γ can be added to the medium simultaneously with the M-CSF/GM-CSF and the CD16 ligand which means that the cytokine may be added, e.g., at the time when the culture of the monocytes is initiated. In such a method, the monocytes to be differentiated by the method of the invention will be cultured in the presence of M-CSF/GM-CSF, the CD16 ligand and IFN-γ for the entire culturing period. Normally, however, the culturing period in the presence of IFN-γ is considerably shorter than the culturing period in the presence of M-CSF/GM-CSF, which means that the IFN-γ is added after the cells have been cultured for 3 days in the presence of M-CSF/GM-CSF, and culturing in the presence of IFN-γ is continued for another 18-72 hours.

Particularly good results have been achieved when the cells are cultured for 6 days in the presence of M-CSF/GM-CSF and the CD16 ligand, pulsed with IFN-γ for 18-24 hours, and then harvested at day 7. The differentiated macrophages may be washed by a buffer which is compatible for use with macrophages, such as Phosphate Buffered Saline (PBS) supplemented with 5% human serum albumin. The Mreg cells can be transferred and stored in a transfusion bag, a glass infusion device or in another closed-system container which allow for the transportation.

The above preparation process results in an immunoregulatory macrophage which is characterized by the expression of certain marker molecules which distinguish the Mreg cells from other regulatory or non-regulatory macrophages. Most significantly, the Mregs for use in a method of the present invention express the markers CD258, DHRS9 and IDO. The combination of these three markers provides a reliable tool for specifically detecting Mregs and separating them from other macrophages.

CD258, which is also referred to in the literature as LIGHT or TNFSF14, is a secreted protein of the TNF superfamily. The human sequence of CD258 can be found under NCBI gene_ID 8740. IDO refers to the Indoleamine 2,3-dioxygenase. The sequence of the human gene encoding this marker can be found under NCBI gene_ID 3620. Synonyms for IDO are IDO1 or INDO. DHRS9 is a retinol dehydrogenase of the SDR family of retinol dehydrogenases. The sequence of the human gene encoding this marker can be found under NCBI gene_ID 10170.

In a preferred embodiment of the invention, immunoregulatory macrophage for use in the method of the invention further expresses at least one of the markers selected from the group consisting of TGFβ1 and PAEP. TGFβ1 refers to the transforming growth factor beta, a multifunctional cytokine belonging to the transforming growth factor superfamily. The sequence of the human gene encoding this marker can be found under NCBI gene_ID 7040. PAEP refers to the progestagen-associated endometrial protein. The sequence of the human gene encoding this marker can be found under NCBI gene_ID 5047.

Since Mregs are macrophages they also express common macrophage markers. Therefore, in a preferred embodiment, the Mreg further expresses at least one of the macrophage markers selected from the group consisting of CD33, CD11b and HLA-DR.

In a particularly preferred embodiment, the Mreg cell to be used according to the invention as one of the following phenotypes:
(1) CD258, DHRS9, IDO;
(2) CD258, DHRS9, IDO, TGFβ1;
(3) CD258, DHRS9, IDO PAEP;
(4) CD258, DHRS9, IDO, TGFβ1, PAEP;
(5) CD258, DHRS9, IDO, TGFβ1, PAEP, CD33;
(6) CD258, DHRS9, IDO, TGFβ1, PAEP, CD33, CD11b;
(7) CD258, DHRS9, IDO, TGFβ1, PAEP, CD33, CD11b, HLA-DR;
(8) CD258, DHRS9, IDO, CD33, CD11b, HLA-DR;
(9) CD258, DHRS9, IDO, CD33, CD11b, HLA-DR, TGFβ1;
(10) CD258, DHRS9, IDO, CD33, CD11b, HLA-DR, PAEP.

An immunoregulatory macrophage that expresses CD258, DHRS9, IDO, TGFβ1 and PAEP is particularly preferred herein.

In a preferred aspect, the Mreg used in the method of the present invention fails to express at least one of the markers Clec-9a, CD10 and CD103. In another preferred aspect, the Mreg used in the method of the present invention fails to express all of the markers Clec-9a, CD10 and CD103. In another preferred aspect, the Mreg used in the method of the present invention expresses at least one of the markers CD38, CD209 and Syndecan-3. In yet another preferred aspect, the Mreg used in the method of the present invention expresses all of the markers CD38, CD209 and Syndecan-3. In another preferred aspect, the Mreg used in the method of the present invention fails to express at least one of the markers Clec-9a, CD10 and CD103, but expresses at least one of the markers CD38, CD209 and Syndecan-3.

The expression of the markers can be determined on the mRNA or protein level. In a particularly preferred embodiment, detection of the markers is made at the transcriptional level. Suitable methods for monitoring gene expression at the transcriptional level include those which allow for the quantitative or semi-quantitative detection of mRNA levels, for example, quantitative RT-PCR (e.g., TaqMan™ RT-PCR), real-time RT-PCR, Northern-Blot analysis or other methods which are generally known in the art.

Detection at the transcriptional level usually requires as a first step the isolation of mRNA from the macrophages to be analysed, e.g., macrophages obtained from a blood sample. Methods for isolating RNA, such as mRNA, are well known in the art and are discussed in detail in the literature (see, for example, Sambrook et al. (1989), Molecular Cloning—A Laboratory Manual, Cold Spring Harbor Laboratory, Cold Spring Harbor, New York and Ausubel et al. (1994), Current Protocols in Molecular Biology, Current Protocols Publishing, New York). Such methods normally involve the lysis of the cells or tissues obtained from the subject to be tested. Cell lysis may be performed by use of detergents which are capable of disrupting the plasma membrane of the cells. For example, buffers containing guanidine thiocyanate and/or SDS may be used for cell lysis. The methods may comprise steps in which the DNA of the cells is enzymatically digested in order to obtain pure RNA without traces of DNA which might interfere with further downstream applications, such as the monitoring of expression levels. Inhibitors of enzymes which lead to the degradation of the RNA may also be added to the lysis buffer. Kits for preparing highly purified RNA are available from several manufacturers, such as Qiagen, Ambion, Stratagene, Clontech, Invitrogen, Promega, and others.

The RNA isolated from the cell or tissue sample by use of commercial kits will normally comprise different types of RNA. Preferably, the RNA obtained from the tissue sample is total RNA comprising mRNA, transfer RNA (tRNA) and ribosomal RNA (rRNA). For the methods of the present invention, it is desirable to enrich the mRNA fraction with respect to fractions of other cellular RNAs. Preferably, the mRNA is separated from other RNA molecules. Methods for enriching or purifying mRNA are known in the art. For example, an affinity chromatography using oligo(dT) or poly(U) coupled to a solid matrix, such as a cellulose or Sephadex™ matrix can be performed, as mRNAs contain a poly(A) tail at their 3' terminus (see, for example, Ausubel et al. (1994), Current Protocols in Molecular Biology, Current Protocols Publishing, New York). Poly(A)+ mRNA which has bound to the affinity matrix can be eluted using 2 mM EDTA/0.1% SDS.

One commonly used method for detecting expression at the transcriptional level is RT-PCR. In this method, an mRNA template is transferred into cDNA by a reverse transcription (RT) reaction. The reverse transcription of the RNA template is catalyzed by a reverse transcriptase, and the reaction can be primed by specific oligonucleotide primers, or, alternatively, by oligo-dT primers. The cDNA is then used as template for a subsequent PCR reaction. In the subsequent PCR step, the cDNA is amplified by use of specific oligonucleotide primers and a polymerase enzyme, e.g., a Taq polymerase. In a preferred embodiment, the RT-PCR reaction is performed as a real-time RT-PCR, which enables the detection and the simultaneous quantification of amplified DNA in real-time. Quantification occurs either as an absolute number of copies or as a relative amount normalized by use of additional gene expression products.

In a further preferred embodiment, a TaqMan RT-PCR is used for determining the expression levels of the markers. The TaqMan RT-PCR is a fluorophore-based RT-PCR method which detects accumulation of a specific, amplified product during PCR. In TaqMan RT-PCR, RNA is first transferred into cDNA by a reverse transcriptase. In the subsequent PCR reaction, a single-stranded oligonucleotide probe is added which is complementary to a segment of 10-60 nucleotides within the DNA template and located between the two PCR primers. A fluorophore and a quencher dye are covalently attached to the 5' and 3' ends of the probe, respectively. Alternatively, the quencher dye can also be attached to an internal nucleotide, while the fluorophore is attached to the 5' or 3' end of the probe or vice versa. The close proximity between fluorophore and quencher dye attached to the probe inhibits fluorescence emission from the fluorophore when said fluorophore is selectively excited. During DNA synthesis in the PCR, the 5' exonuclease activity of the Taq polymerase cleaves the oligonucleotide probe which is hybridized to the template DNA, thereby spatially separating the fluorophore and the quencher dye. Fluorescence is detected during PCR cycling; it is directly proportional to the fluorophore released and the 0 amount of DNA template present in the PCR. Every fluorophore-quencher pair known in the art can be used in the methods of the present invention. Examples of suitable fluorophores are FAM (6-carboxyfluorescin), TET (tetrachlorofluorescin) or VIC. A suitable quencher dye is TAMRA (tetramethyl-rhodamine). The construction and labeling of oligonucleotides to be used as probes in a TaqMan approach are described in great detail in the literature. A TaqMan reaction can be carried out using, e.g., the ABI PRISM 7700 system (Perkin-Elmer/Applied Biosystems, Foster City, Calif., USA), or the Lightcycler system (Roche Molecular Biochemicals, Manheim, Germany).

A microarray is another commonly used tool in expression profiling. A microarray refers to the orderly arrangement of spatially resolved probes, for example nucleic acid probes, on a substrate. Such arrays can contain at least one, and preferably more than one, oligonucleotide which is complementary to the gene of interest, e.g., the CD258, DHRS9, IDO genes, and thus hybridizes to the respective gene sequence or its transcript. The substrate is preferably a solid substrate having a surface with a plurality of probes attached in different known locations (spots). The spots on a microarray are normally either printed on the microarrays or synthesized by photolithography or by ink-jet printing. On a common microarray, there may be several thousand spots, wherein each of the spots may contain a high number of identical probes, such as nucleic acid fragments or oligonucleotides. Such microarrays typically have a density of at least 100 oligonucleotides or fragments per $cm^2$. In certain embodiments the arrays can have a density of about at least 500, at least 1000, at least 10,000, at least $10^5$, at least $10^6$, at least $10^7$ oligonucleotides or fragments per $cm^2$. The support can be a glass or plastic slide or membrane on the surface of which the probes are attached at fixed locations or spots.

The primers or probes used in the PCR or RT-PCR reactions mentioned herein will be designed to allow the specific hybridization to and the subsequent amplification of the target sequence within the respective marker gene, e.g., the CD258, DHRS9, or IDO gene. Based on the present disclosure, the skilled person will be readily able to design oligonucleotide primers and/or probes which can be used for detecting the expression of the respective Treg marker gene. Methods for designing sequence-specific oligonucleotide primers for PCR or RT-PCR are discussed in great detail in the scientific literature, e.g., in Dieffenbach and Dveksler, "PCR Primer", A Laboratory Manual, Cold Spring Harbor Laboratory Press, New York, 2003. The parameters to be considered when designing PCR primers include, for example, the number of nucleotides, the G/C content of the primer, the melting temperature, the presence of complementary nucleotides which may lead to secondary structures, and the like. The oligonucleotides for use in the methods of the present invention preferably have a length of at least 8 nucleotides, more preferably at least 10, 12, 14, 16, 18, 20, 22, 24, 26, 28, 30, 32, 34, 36, 38, 40, 42, 44, 46, 48 or 50 nucleotides. The oligonucleotide primers can be prepared by any suitable technique known in the art. For example, they may be derived synthetically, for example by the phosphoamidite method. Apart from oligomers or polymers which contain the naturally occurring nucleotide bases adenine, thymine (uridine), cytosine or guanine, oligonucleotide primers of the invention may also include modified bases, such as 5-methylcytosine, 5-hydroxymethylcytosine, and the like.

Probes and primers for the detection of the markers referred to herein can be designed according to routine methods based on the human genomic sequence of the respective markers. The sequences of these markers are known in the art and can be found in sequence databases. It will be appreciated that probes and primers do not necessarily have to show full complementarity to the genomic sequence over their whole length. A limited number of sequence deviations is acceptable as long as the probes and primers exhibit specific binding to the respective mRNA. Normally, the overall sequence identity of the probe and primer to its cognate mRNA molecule will be at least about 90%, 95%, 96%, 97%, 98%, 99% or more. Computer programs for determining the degree of identity between nucleotide sequences are available, e.g., in the Wisconsin Sequence Analysis Package, Version 8 (available from Genetics Computer Group, Madison, USA) and include, e.g., the programs BESTFIT, FASTA and GAP, which are based on the algorithm of Smith and Waterman. These programs can be used with the standard parameters, as recommended by the manufacturer.

Where high levels of mRNA of the markers, e.g., CD258, DHRS9 and IDO, are detected, it can be assumed that this cell is an Mreg. While it is possible that also non-Mreg cells, such as resting macrophages, may express one or more than one of the markers indicated above to some degree, such expression will be comparatively low. According to the invention, it is hence preferred that the expression of the markers by non-Mreg cells, in particular by a resting macrophage, is used as a negative control. Measuring marker expression at an RNA level which is at least about 50%, at least about 75%, at least about 150%, at least about 200%, at least about 250%, at least about 300%, at least about 350%, at least about 400%, at least about 450%, at least about 500%, at least about 550%, at least about 600%, at least about 750%, or at least about 1000% higher than the respective amounts in the negative control, i.e., in the resting macrophages, clearly indicates that the tested cell is an Mreg cell.

In yet another particularly preferred embodiment, detection of the Mreg markers, e.g., CD258, DHRS9 and IDO, involves the detection of marker gene expression at the translational level. This means that the protein level of the respective Mreg marker, such as CD258, DHRS9 and IDO, is determined. Mreg protein levels may be determined by any suitable method which is able to specifically detect the marker protein in a biological sample. The detection of the protein may be based on a molecule that binds specifically to the protein or it may be based on the separation of the protein from other proteins that are present in the sample. Molecules that specifically bind to Treg marker proteins include antibodies and antibody fragments with binding activity for the Mreg markers. Numerous antibodies have been prepared and can be commercially chased which are directed to Mreg marker proteins like CD258, DHRS9 and IDO. Such antibodies or fragments thereof may be used for detection of the Mreg marker proteins in a Western blot, quantitative Western blot, enzyme-linked immunosorbent-assay (ELISA), polarization analysis, (quantitative) surface plasmon resonance (SPR), or in immunohistochemical methods, including quantitative electron microscopic methods. In a particularly preferred embodiment of the invention, the detection of the markers involves an ELISA. Other methods which are able to detect specific binding include, for example, fluorescence resonance energy transfer (FRET). Methods which allow the quantitative detection of the Treg marker protein by separating the protein from other components in the biological sample include quantitative mass spectrometric methods, electrophoretic methods, such as two-dimensional gel electrophoresis, and chromatographic methods, such as size-exclusion chromatography or ion-exchange chromatography.

As stated above, it is possible that also non-Mreg cells may produce the Mreg markers mentioned above, e.g., CD258, DHRS9 and IDO, in low amounts. Accordingly, protein levels of non-Mreg cells, such as a non-regulatory macrophage, should also be measured to provide a negative control. If the protein levels for tested cells reveal that marker expression is higher than the negative control, this allows the conclusion that the tested cell is a Mreg. Specifically, measuring a marker expression at the protein level which is at least about 50%, at least about 75%, at least about 150%, at least about 200%, at least about 250%, at least about 300%, at least about 350%, at least about 400%, at least about 450%, at least about 500%, at least about 550%, at least about 600%, at least about 750%, or at least about 1000% higher than the respective amounts in the negative control, i.e., in the non-Mreg cell, such as a non-regulatory macrophage, clearly indicates that the tested cell is an Mreg cell.

In an even more preferred embodiment of the invention, detection of the Mreg markers involves flow cytometry. Flow cytometry is a widely used method for analyzing the expression of cell surface markers and intracellular molecules. It is routinely used for applications like cell counting, cell sorting, and biomarker profiling. In particular it can be used for defining different cell types in a heterogeneous cell population. Flow cytometry is predominantly used to measure fluorescence intensity produced by fluorescent-labeled antibodies that detect markers on the cell surface. Although it can also be used for the detection of intracellular markers, such detection is less desirable, since the antibody must permeate the cell which normally kills the cell. This prevents the detection of intracellular markers for cell sorting applications which aims at the provision of viable homogeneous cell populations.

In another preferred embodiment, the Mreg cell for use in the method of the present invention has the ability to induce CD25+ FoxP3+ iTregs. The ability to induce Tregs can be tested by when co-culturing Mregs for 5 days with allogeneic T cells at a 1:2 ratio.

BRIEF DESCRIPTION OF THE FIGURES

FIG. 2A shows that strong DHSR9 mRNA expression was detected in Mregs by RT-qPCR, but not comparator macrophage types (n=6; mean±SD).

FIG. 2B shows the results of immunoblotting demonstrating that DHSR9 protein expression distinguishes Mregs from comparator macrophages.

FIG. 2C shows expression of TNFSF14/CD258 mRNA in a panel of comparator macrophages quantified by microarray analysis (n=3; mean±SD).

FIG. 2D shows cell-surface expression of CD258 by human Mregs detected by flow cytometry.

FIG. 2E illustrates an experimental system to show that direct interaction of naive CD25$^-$ FoxP3$^-$ CD4$^+$ T cells with human Mregs leads to their conversion into activated CD25$^+$ FoxP3$^+$ CD4$^+$ T cells.

FIG. 2F shows iTregs generated from naive CD25$^-$ FoxP3$^-$ CD4$^+$ T cells through interaction with human Mregs when cocultured in a 1:2 ratio.

FIG. 2G shows expression of IDO mRNA in a panel of comparator macrophages quantified by microarray analysis (n=3; mean±SD).

FIG. 2H shows expression of IDO by human Mregs detected by intracellular staining and flow cytometry.

FIG. 2I shows expression of PAEP mRNA in a panel of comparator macrophages quantified by microarray analysis (n=3; mean±SD).

FIG. 2J shows that neutralisation of secreted PAEP protein with a neutralising antibody against PAEP led to a significant reduction in iTreg generation.

FIG. 2K shows expression of TGFβ1 mRNA in a panel of comparator macrophages quantified by microarray analysis (n=3; mean±SD).

FIG. 2L shows 24-hour secretion of TGFβ1 by human Mregs and comparator macrophages.

FIG. 2M shows a comparison of Mregs with PCMOs in terms of Treg induction.

EXAMPLES

Figure 1:
FIG. 1 shows the results of treating leg ulcers in a patient suffering from peripheral artery disease (PAD) by injection of 1×10$^7$ Mregs.

The Mregs were manufactured in accordance with current GMP principles for the production of sterile medicinal products. Attention is paid at every processing step that products, materials and equipment are protected against contamination and impurities.

Example 1: Preparation of Mregs

A first Mreg preparation ("Mreg A") was prepared according to a modified protocol of Hutchinson. Healthy human donors were subjected to leukapheresis to collect peripheral blood mononuclear cells (PBMC) which are used as starting material for Mreg generation. All donors were screened for relevant disease markers, including infectious diseases, not more than 30 days prior to leukapheresis. Donors were re-screened for the same disease markers on the day of leukapheresis. Leukapheresis was performed using the Terumo BCT Cobe Spectra device or equivalent. CD14+ monocytes were isolated from the leukapheresis product using the Miltenyi CliniMACS® system in accordance with the manufacturer's instructions.

Plastic-adherent monocytes were plated at a density of $35 \times 10^6$ monocytes/175 cm$^2$ culture flask (Cell+ T175 flask; Sarstedt) in 30 ml RPMI 1640-based medium without phenol red (Lonza) supplemented with 10% human AB serum (Lonza), 2 mM L-glutamine (Lonza), 100 U/ml penicillin, 10 μg/ml streptomycin (Lonza), and recombinant human M-CSF (RSCD Systems) at a final concentration of 5 ng/ml carried on 0.1% human serum albumin (Aventi). The cells were cultured for 6 days with complete medium exchanges on days 1, 2, and 4. On day 6, cultures were stimulated with 25 ng/ml recombinant human IFN-γ (Imukin; Boehringer Ingelheim). On day 7, the adherent cell fraction was recovered by trypsin-EDTA treatment (TrpE Express without Phenol Red; Invitrogen) followed by gentle scraping. Mregs from all flasks were pooled and resuspended in a physiological saline solution containing 5% human albumin.

A second Mreg preparation ("Mreg B") was prepared based on the protocol described in Example 1 of PCT/EP2017/055839. Healthy human donors were subjected to leukapheresis to collect peripheral blood mononuclear cells (PBMC) which are used as starting material for Mreg generation. All donors were screened for relevant disease markers, including infectious diseases, not more than 30 days prior to leukapheresis. Donors were re-screened for the same disease markers on the day of leukapheresis. Leukapheresis was performed using the Terumo BCT Cobe Spectra device or equivalent.

CD14+ monocytes were isolated from the leukapheresis product using the Miltenyi CliniMACS® system in accordance with the manufacturer's instructions. Briefly, the leukapheresis product was transferred into a bag which was filled with PBS/EDTA-buffer containing 0.5% human serum albumin (HSA). The cells were washed once before labelling with CliniMACS® CD14 reagent according to the manufacturer's instructions. The labelled cell suspension was connected to a sterile tubing set and installed on the CliniMACS® device in order to isolate CD14+ monocytes by magnetic separation. The positively-isolated CD14+ monocyte fraction was washed with culture medium to remove the CliniMACS® separation buffer. The isolated CD14+ monocytes were re-suspended at a density of $10^6$ cells/ml in RPMI medium that had been supplemented with 10% male-only human AB serum (pooled and heat-inactivated), 2 mM GlutaMAX™ and 25 ng/ml recombinant human monocyte colony-stimulating factor (M-CSF). This monocyte suspension was distributed into Miltenyi® cell differentiation bags, such that each bag was seeded with $1 \times 10^6$ cells/cm$^2$ internal surface area. For cultivation, the differentiation bags were laid flat on shelves within an incubator which was set to 36-38° C., 5±1% CO$_2$,≥60% humidity. The monocytes were allowed to precipitate onto the lower leaf of the culture bags over the course of 1 day. On day 1, the bags were inverted to allow monocytes to adhere to the opposite leaf. The cultures were maintained in the incubator for a further 5 days. To induce the final differentiation of monocytes into Mregs and to induce indoleamine 2,3-dioxygenase (IDO) expression, monocytes were stimulated by the addition of 25 ng/ml IFN-γ. After the addition of IFN-γ, the differentiation bags were inverted another time. The bags were then incubated for a further 18-24 h at 36-38° C., 5±1% CO2,≅60% humidity. On day 7, the differentiated Mregs were harvested. Cells from all parallel culture bags were pooled and washed prior to phenotypic and functional analyses.

Example 2: Phenotypic Characterization of Mregs

"Mreg A" cells obtained from Example 1 were tested for the expression of different markers. Specifically, the expression of different markers potentially having specificity for Mregs was evaluated by RT-PCR.

Figure 2A:
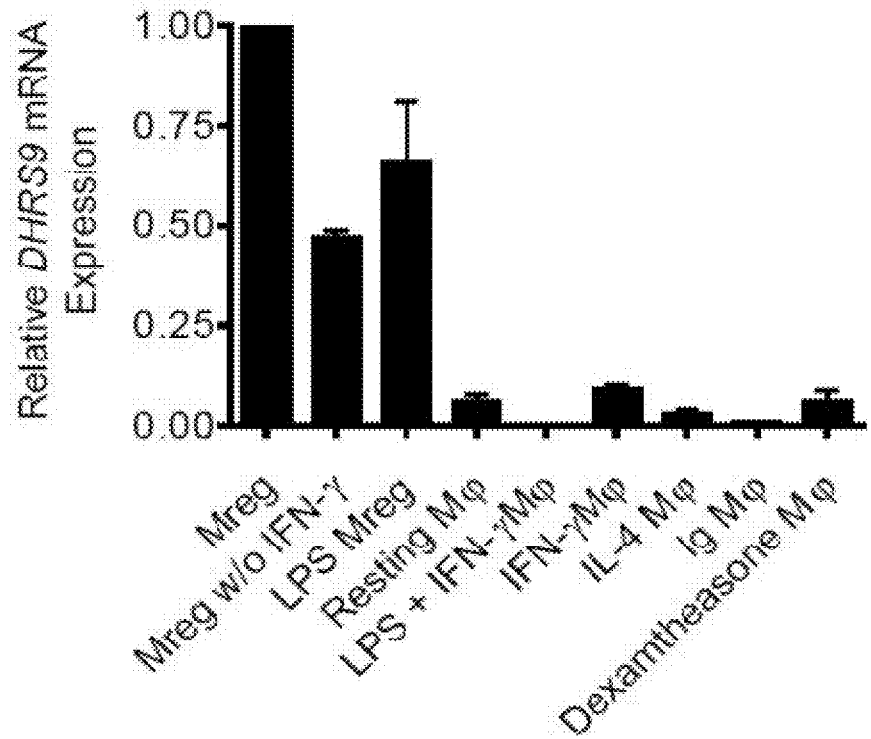
FIGS. 2A-2M specifies the phenotype and specialized functional characteristics of human Mregs.
Figure 2B:
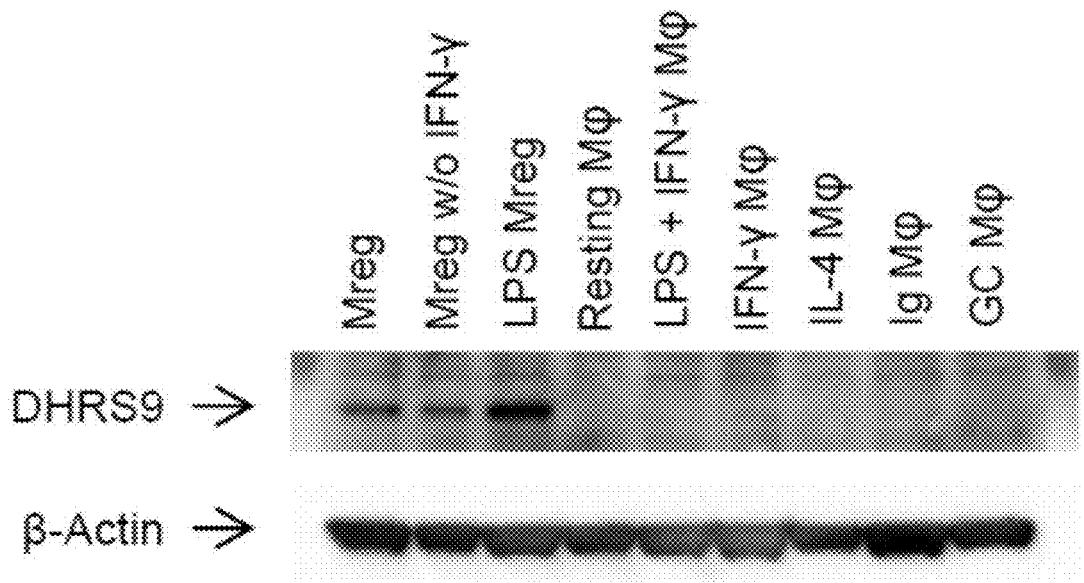

DHRS9: It could be shown that DHSR9 expression distinguishes human Mregs from monocyte-derived macrophages and dendritic cells. Strong DHSR9 mRNA expression was detected in Mregs, but not comparator macrophage types (n=6; mean±SD), see FIG. 2A. Immunoblotting with a custom-made rabbit anti-DHSR9 pAb demonstrated that DHSR9 protein expression distinguishes Mregs from comparator macrophages, see FIG. 2B.

Figure 2C:
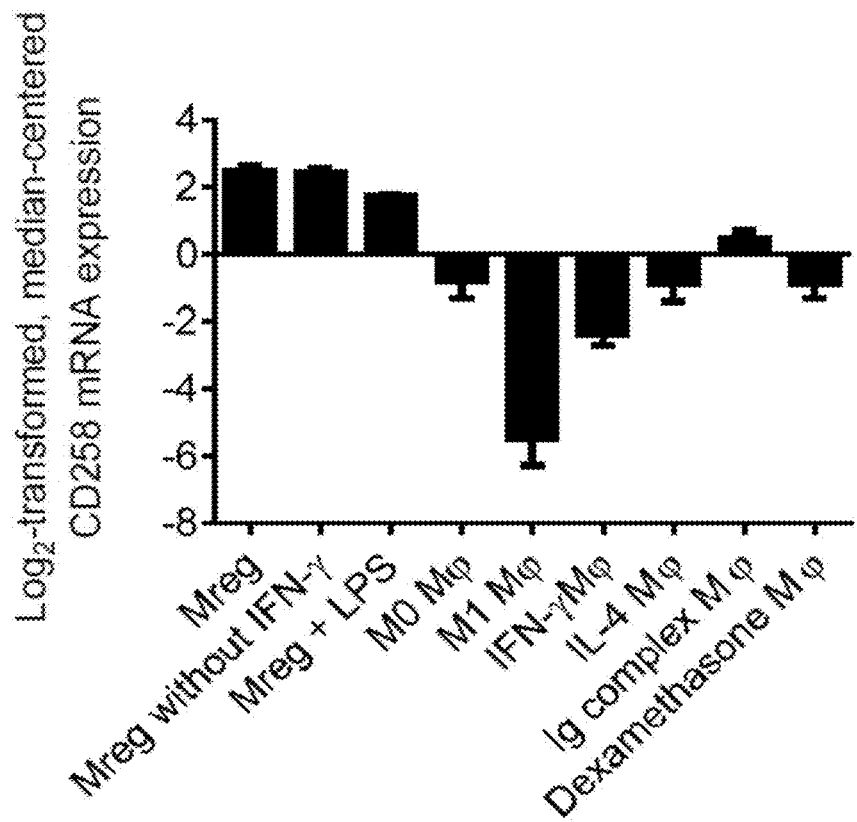
Figure 2D:
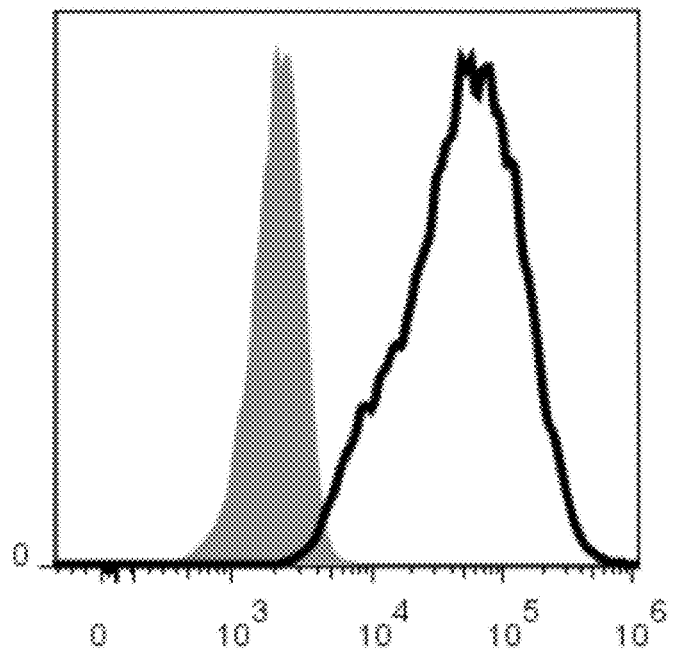
Figure 2E:
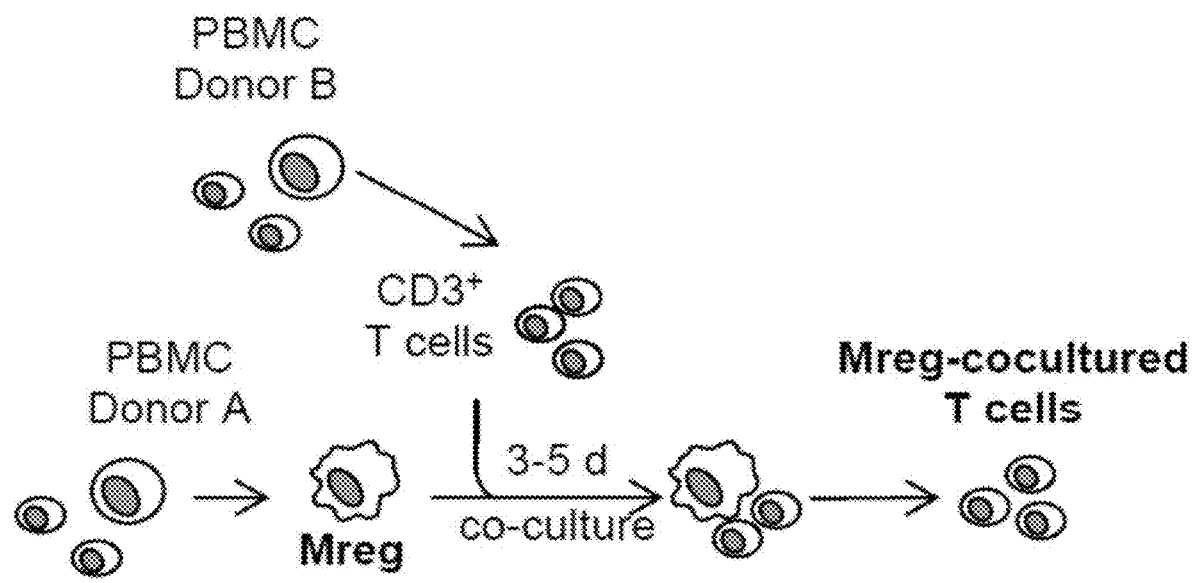

CD258: It could be found that CD258 (TNFSF14) is an informative marker of human Mregs. TNFSF14 mRNA expression was detected in Mregs, but not in comparator macrophages (n=3; mean±SD), see FIG. 2C.

Figure 2F:
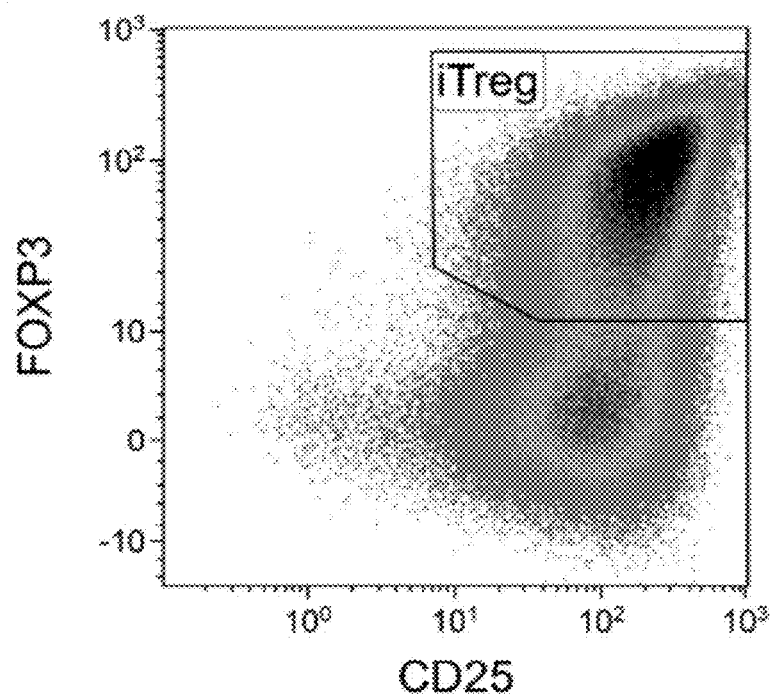
Figure 2G:
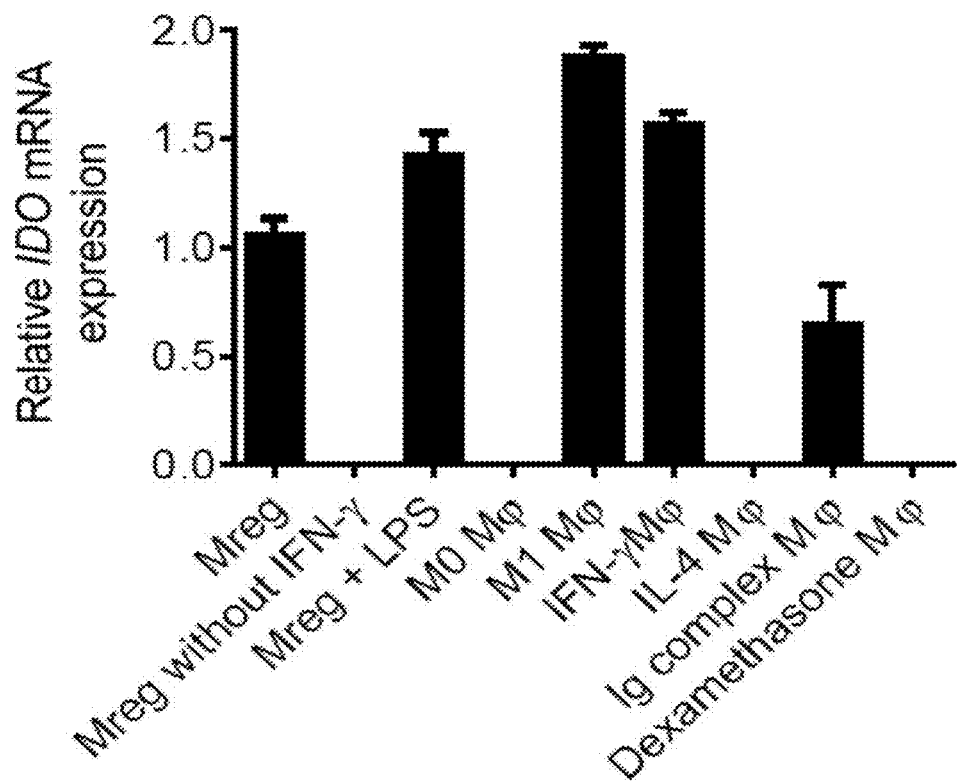
Figure 2H:
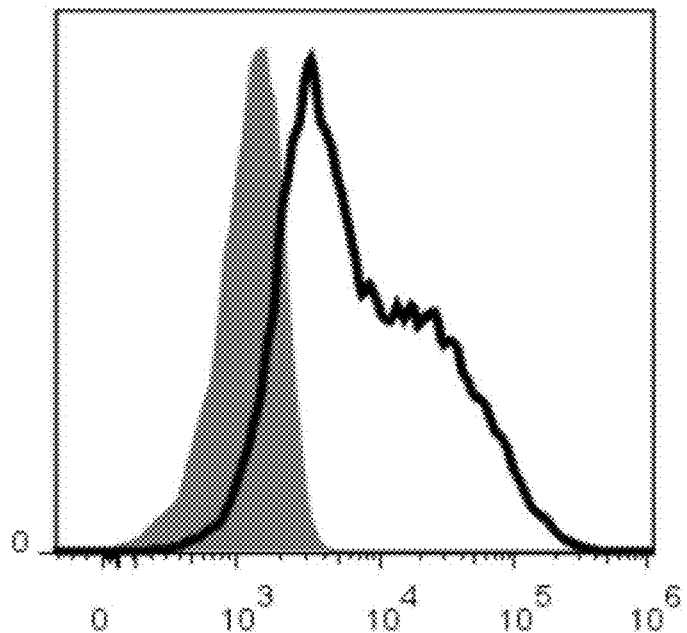

IDO: Mregs were found to express IDO, while comparator macrophages do not express this marker. Expression of IDO by Mregs was detected by flow cytometry, see FIG. 2H.

Figure 2I:
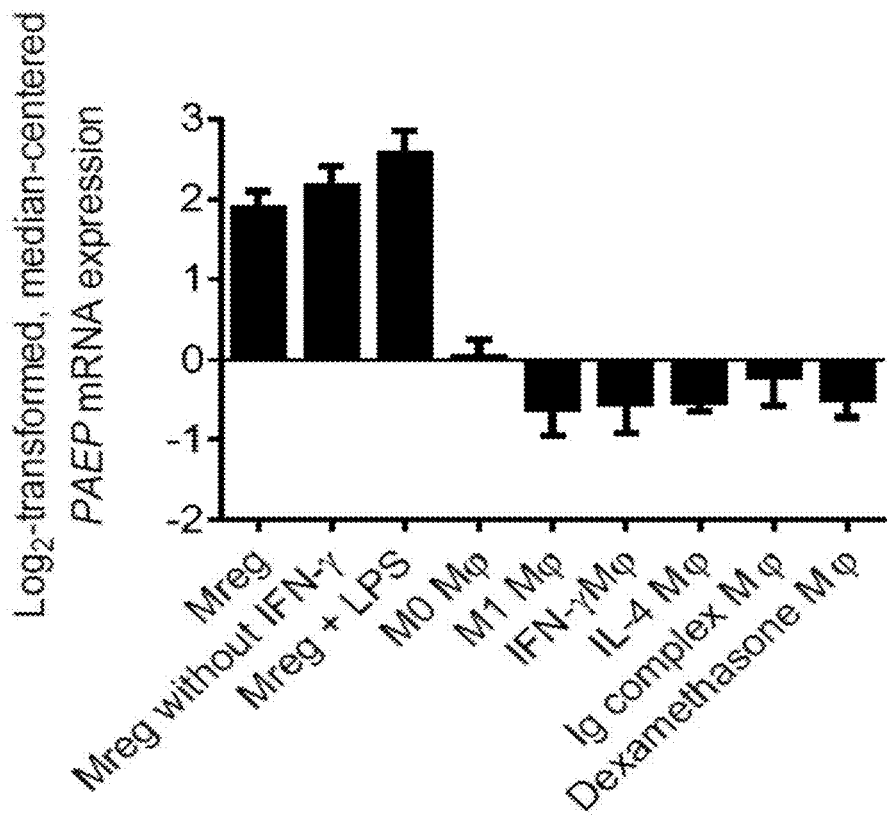
Figure 2J:
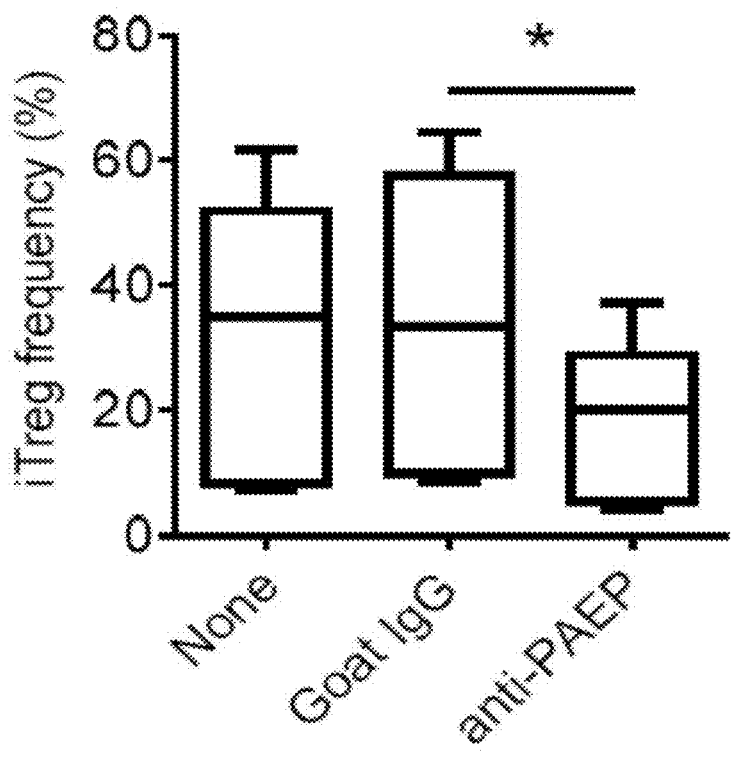

PAEP: Mregs were found to express PAEP, while comparator macrophages do not express this marker. FIG. 2I shows the expression of PAEP mRNA in a panel of comparator macrophages (n=3; mean±SD).

Figure 2K:
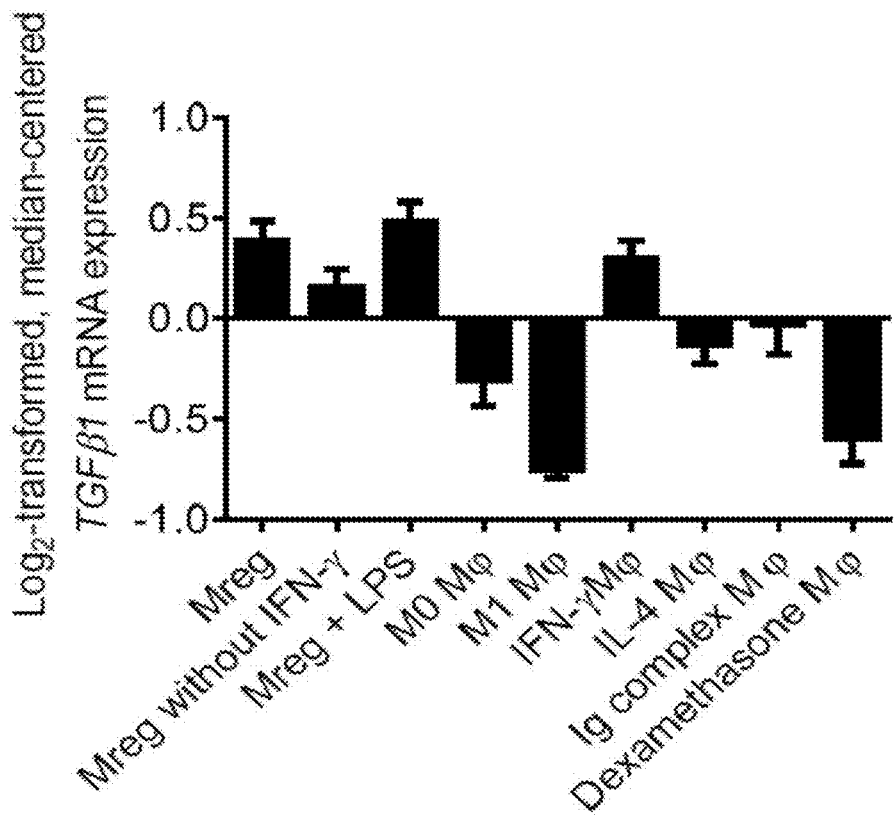
Figure 2L:
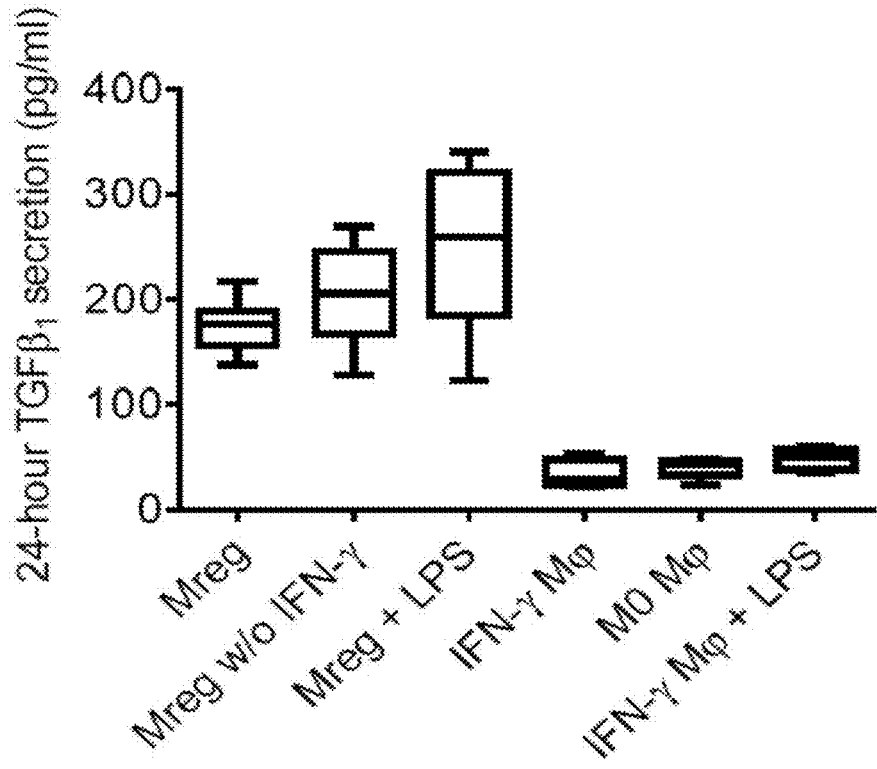

TGFβ1: Mregs were found to express TGFβ1, while comparator macrophages do not express this marker. FIG. 2K shows the expression of TGFβ1mRNA in a panel of comparator macrophages (n=3; mean±SD).

Figure 2M:
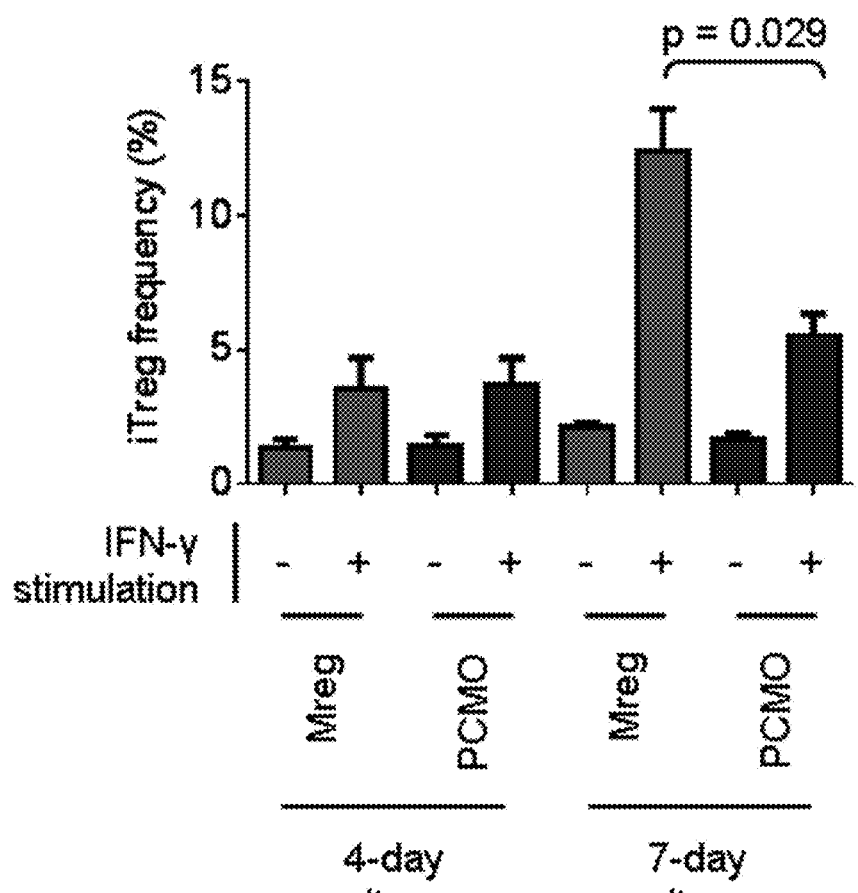

Tregs induction: Human Mregs generated from peripheral blood CD14+ monocytes were cocultured for 5 days with allogeneic T cells at a 1:2 ratio. The T cells were then analysed by flow cytometry and functional assays. T cells cocultured with allogeneic Mregs for 5 days were enriched for T cell-suppressive CD25+ FoxP3+ iTregs (FIG. 2F) which were readily discriminated from CD25+FoxP3−/low polyclonally activated T cells generated by stimulation with αCD3/αCD28 beads for 5 days. Mregs were compared to PCMO cells. The results are shown in FIG. 2M. It can be seen that the ability of inducing Tregs is limited to Mregs.

Example 3: Mregs for Treating Leg Ulcers

A 78-year old male patient suffering from peripheral artery disease (PAD) of stadium IIa in the right limb and stadium III in the left limb had undergone multiple percutaneous transluminal angioplasty (PTA) procedures and a bypass operation of the Arteria femoralis communis (AFC) and Arteria femoralis superficialis (AFS), as well as the Arteria politea left, respectively. He suffered from intensive pain episodes while walking and at rest, especially during the night.

The patient was treated with an Mreg preparation ("Mreg A") obtained from Example 1. Specifically, $1\times10^7$ Mregs diluted in 12 ml of 5% human serum albumin were injected into six injection sites along the lateral part of the ulcer, i.e., 2 ml per injection site. Where muscle tissue beneath the wound was accessible, the injection was given intramuscularly. Otherwise the injection was given subcutaneously. No additional treatments were performed thereafter. The wound was kept sterile with dry bandages that were changed daily.

Results: The clinical follow up of the patient shows a significant improvement in terms of wound closure over time. Clinically, night pains completely disappeared with no ischemic pain at rest. This improvement was first observed 3 months after injection of the Mregs. Walking distance improved to more than 2 km. The results of the treatment are depicted in FIG. 1.

Example 4: Mregs for Treating PAD

A 64-year old female patient suffering from diabetes mellitus with an extended arteriopathic component and peripheral artery disease (PAD) of stadium IV in the right limb was presented. She had developed a heel ulcer with a bare bone. No Arteria femoralis superficialis (AFS) or crural diffuse vessel collateralization existed anymore. No operative therapeutic interventions were possible, due to lack of crural connecting vessels. Transfemoral amputation was considered as the last treatment option.

The patient was treated with an Mreg preparation ("Mreg A") obtained from Example 1. In total 50.000 Mregs were administered as described in Example 3 at 5 different identified (angiography) critical points. No additional treatments were performed thereafter. The wound was kept sterile and the bandages were changed daily.

Results: Clinical follow up of the patient demonstrated significant improvement of wound healing two weeks after injection. After 3 months wound healing was fully completed and the blood circulation of the right leg was compensated. The formation of additional collateral vessels was demonstrated via angiography. Transfemoral amputation was avoided.

LITERATURE

[1] Geissler E K, Hutchinson J A. Cell therapy as a strategy to minimize maintenance immunosuppression in solid organ transplant recipients. Curr Opin Organ Transplant 2013; 18: 408-15.

[2] Tang Q, Bluestone J A, Kang S M. CD4(+) Foxp3(+) regulatory T cell therapy in transplantation. J Mol Cell Biol 2012; 4: 11-21.

[3] Moreau A, Varey E, Bouchet-Delbos L, et al. Cell therapy using tolerogenic dendritic cells in transplantation. Transplant Res 2012; 1: 13.

[4] Broichhausen C, Riquelme P, Geissler E K, et al. Regulatory macrophages as therapeutic targets and therapeutic agent in solid organ transplantation. Curr Opin Organ Transplant 2012; 17: 332-42.

[5] Hutchinson J A, Riquelme P, Sawitzki B, et al. Cutting edge: immunological consequences and trafficking of human regulatory macrophages administered to renal transplant recipients. J Immunol 2011; 187: 2072-8.

[6] Hutchinson J A, Riquelme P, Brem-Exner B G, et al. Tranplant acceptance-inducing cells as an immune-conditioning therapy in renal transplantation. Transpl Int 2008; 21: 728-41.

[7] Hutchinson J A, Brem-Exner B G, Riquelme P, et al. A cell-based approach to the minimization of immunosuppression in renal transplantation. Transpl Int 2008; 21: 742-54.

[8] Hutchinson J A, Roelen D, Riquelme P, et al. Preoperative treatment of a pre-sensitized kidney transplant recipient with donor-derived transplant acceptance-inducing cells. Transpl Int 2008; 21: 808-13.

[9] Hutchinson J A, Govert F, Riquelme P, et al. Administration of donor-derived transplant acceptance-inducing cells to the recipients of renal transplants from deceased donors is technically feasible. Clin Transplant 2009; 23: 140-5.

The invention claimed is:

1. A method of treating micro-or macroangiopathies of lower limbs or inducing wound healing in a subject, comprising administering an immunoregulatory macrophage expressing the markers CD258, DHRS9 and IDO to the subject.

2. The method of claim 1, wherein said macrophage expresses the markers CD258, DHRS9, IDO and TGFβ1.

3. The method of claim 1, wherein said macrophage expresses the markers CD258, DHRS9, IDO, TGFβ1 and PAEP.

4. The method of claim 1, wherein said macrophage further expresses at least one of the markers selected from the group consisting of macrophage lineage markers CD33, CD11b and HLA-DR.

5. The method of claim 1, wherein said micro- or macroangiopathies are diabetic micro- or macroangiopathies.

6. The method of claim 1, wherein said method comprises the administration of between $1\times10^5$ to $1\times10^7$ macrophages to the subject.

7. The method of claim 1, wherein the wound is an ulcer and said method comprises the administration of macrophages directly into the ulcer by subcutaneous or intramuscular injection.

8. The method of claim 1, wherein said microangiopathy is selected from the group consisting of angiitis, arteritis, angiodysplasia, atrophy blanche, dermatosclerosis, Determann syndrome, diabetic angiopathy, endangiitis obliterans, erythromelalgia, fibro muscular dysplasia, malum perforans, Mönckeberg Sclerosis, Osler's disease, compartment syndrome, Paget-von-Schroetter syndrome, Raynaud's syndrome, and leg ulcers.

9. The method of claim 1, wherein said macroangiopathy is selected from the group consisting of aneurysm, dissection, atherosclerosis, atherothrombosis, peripheral arterial occlusive disease (PAD), claudicatio intermittens, necrosis and gangrene, vascular malformation, Leriche syndrome, and compression syndrome.

10. The method of claim 1, wherein said subject is afflicted with diabetic mellitus.

11. The method of claim 1, comprising administering to the subject a pharmaceutical composition comprising said immunoregulatory macrophage expressing the markers CD258, DHRS9 and IDO.

12. A pharmaceutical composition comprising an immunoregulatory macrophage expressing the markers CD258, DHRS9, and IDO.

13. The pharmaceutical composition of claim 12, wherein said immunoregulatory macrophage expresses the markers CD258, DHRS9, IDO and TGFβ1.

14. The pharmaceutical composition of claim 12, wherein said immunoregulatory macrophage expresses the markers CD258, DHRS9, IDO, TGFβ1 and PAEP.

15. The pharmaceutical composition of claim 12, wherein said immunoregulatory macrophage expresses the markers CD258, DHRS9, IDO, TGFβ1 and PAEP.

* * * * *